United States Patent
Bu et al.

(10) Patent No.: US 11,733,199 B2
(45) Date of Patent: Aug. 22, 2023

(54) FABRICATION METHOD OF ENZYME-FREE GLUCOSE SENSOR AND USE OF ENZYME-FREE GLUCOSE SENSOR FABRICATED BY THE SAME

(71) Applicant: Jiangsu University, Jiangsu (CN)

(72) Inventors: Quan Bu, Jiangsu (CN); Jin Cai, Jiangsu (CN); Hairong Long, Jiangsu (CN); Mei Wang, Jiangsu (CN); Hanping Mao, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days.

(21) Appl. No.: 17/610,443

(22) PCT Filed: Apr. 30, 2021

(86) PCT No.: PCT/CN2021/091372
§ 371 (c)(1),
(2) Date: Nov. 11, 2021

(87) PCT Pub. No.: WO2022/062409
PCT Pub. Date: Mar. 31, 2022

(65) Prior Publication Data
US 2022/0341868 A1    Oct. 27, 2022

(30) Foreign Application Priority Data
Sep. 24, 2020 (CN) .................. 202011013417.3

(51) Int. Cl.
*G01N 27/327* (2006.01)
*G01N 27/30* (2006.01)
*G01N 27/416* (2006.01)

(52) U.S. Cl.
CPC ....... *G01N 27/3277* (2013.01); *G01N 27/308* (2013.01); *G01N 27/3278* (2013.01); *G01N 27/4163* (2013.01)

(58) Field of Classification Search
CPC ............ G01N 27/3277; G01N 27/308; G01N 27/3278; G01N 27/4163; G01N 27/30
See application file for complete search history.

(56) References Cited

U.S. PATENT DOCUMENTS

2019/0310223 A1   10/2019   Smith et al.

FOREIGN PATENT DOCUMENTS

| CN | 101315345 | 12/2008 |
| CN | 103424446 | 12/2013 |

(Continued)

OTHER PUBLICATIONS

Online Encyclopedia Britannica definition of "calcination", downloaded Dec. 28, 2022, https://www.britannica.com/technology/calcination (Year: 2022).*

(Continued)

*Primary Examiner* — Alexander S Noguerola
(74) *Attorney, Agent, or Firm* — JCIP Global Inc.

(57) ABSTRACT

The present invention relates to the technical field of glucose detection, and in particular to an enzyme-free glucose sensor and a fabrication method and use thereof. In the present invention, *Magnolia grandiflora* L. leaves are used as a carbon-based catalyst, which serve as a base material to well disperse nickel atoms and improve the catalytic activity of a material. A prepared Ni@NSiC nano-molecular layer is used to modify a pretreated white glassy carbon electrode (GCE) to obtain a highly-active material-modified working electrode Ni@NSiC/GCE, and then glucose is detected through cyclic voltammetry (CV) and chronoamperometry (CA).

8 Claims, 5 Drawing Sheets

(56) References Cited

FOREIGN PATENT DOCUMENTS

| CN | 104237345 | 12/2014 |
|---|---|---|
| CN | 104777203 | 7/2015 |
| CN | 106290498 | 1/2017 |
| CN | 106872545 | 6/2017 |
| CN | 107315043 | 11/2017 |
| CN | 108007998 | 5/2018 |
| CN | 108414589 | 8/2018 |
| CN | 110208344 | 9/2019 |
| CN | 110779974 | 2/2020 |
| CN | 111505078 | 8/2020 |
| CN | 111537589 | 8/2020 |
| CN | 112010359 | 12/2020 |
| CN | 112285174 | 1/2021 |

OTHER PUBLICATIONS

Michael Posteck, Electron Microscopy of Silicon Deposits in Follar Idioblasts of Magnolia Grandiflora, Proc Electron Micros Soc Am, vol. 1976, 34,pp. 374-375 (Year: 1976).*

Michael Posteck, "The Occurrence of Silica in the Leaves of *Magnolia grandiflora* L.," Botanical Gazette, Mar. 1981, vol. 142, No. 1, pp. 124-134 (Year: 1981).*

Postek, Michael Thomas Jr, "Ontogeny and Ultrastructure of the Leaf of *Magnolia grandiflora* L." (1980). LSU Historical Dissertations and Theses. 3534 (Year: 1980).*

Firdaus et al., "Preparation and Characterization of Active $SiO_2$ from Cymbopogon citratus Ash Calcined at Different Temperature," (2016) BioResources 11(1), 2839-2849 (Year: 2016).*

Ratnawulan et al., "Characterization of Silica Sand Due to The Influence of Calcination Temperature," IOP Conf. Series: Materials Science and Engineering 335 (2018) 012008 (Year: 2018).*

Cui et al. , "Single-Step Formation of Ni Nanoparticle-Modified Graphene-Diamond Hybrid Electrodes for Electrochemical Glucose Detection," Sensor 2019, 19, 2979 (Year: 2019).*

Guo et al, "Ni/CdS Bifunctional Ti@$TiO_2$ Core-Shell Nanowire Electrode for High-Performance Nonenzymatic Glucose Sensing," Anal. Chem. 2014, 86, 876-883 (Year: 2014).*

Hathoot et al., "Voltammetric simultaneous determination of glucose, ascorbic acid and dopamine on glassy carbon electrode modified byNiNPs@poly 1,5-diaminonaphthalene," Electrochimica Acta 85 (2012) 531-537 (Year: 2012).*

Karimi-Maleh et al., "Palladium-Nickel nanoparticles decorated on Functionalized-MWCNT for high precision non-enzymatic glucose sensing," Materials Chemistry and Physics 250 (2020 (Year: 2020).*

A. Okhokhonin et al., "Enzymeless Electrochemical Glucose Sensor Based on Carboxylated Multiwalled Carbon Nanotubes Decorated with Nickel (II) Electrocatalyst and Self-assembled Molecularly Imprinted Polyethylenimine," Electroanalysis, vol. 33, Issue 1, Jul. 28, 2020, pp. 1-8.

Zhenyuan Ji et al., "One-step thermal synthesis of nickel nanoparticles modified graphene sheets for enzymeless glucose detection," Journal of colloid and interface science, vol. 506, Jul. 2017, pp. 678-684.

Ensiyeh Sharifi et al., "Shape-dependent electron transfer kinetics and catalytic activity of NiO nanoparticles immobilized onto DNA modified electrode: fabrication of highly sensitive enzymeless glucose sensor," Biosensors & Bioelectronics, vol. 56, Jan. 2014, pp. 313-319.

Xiangheng Niu et al., "Recent advances in non enzymatic electrochemical glucose sensors based on non-precious transition metal materials: opportunities and challenges," RSC Advances, vol. 6, Issue 88, Aug. 2016, p. 84893-84905.

Mamun Jamal et al., "Shell@Core Coaxial NiO@Ni Nanowire Arrays as High Performance Enzymeless Glucose Sensor," Journal of The Electrochemical Society, vol. 160, Issue 11, Sep. 2013, pp. B207-B212.

Wei Wang et al., "A Novel Non-Enzymatic Glucose Sensor Based on Nickel (II) Oxide Electrospun Nanofibers," Journal of Nanoscience and Nanotechnology, vol. 10, Nov. 2010, pp. 7537-7540.

Xiangheng Niu et al., "Highly Sensitive and Selective Nonenzymatic Detection of Glucose Using Three-Dimensional Porous Nickel Nanostructures," Analytical Chemistry vol. 85, Issue 7, Mar. 2013, pp. 3561-3569.

Sun, Kang et al., "Microporous activated carbons from coconut shells produced by self-activation using the pyrolysis gases produced from them, that have an excellent electric double layer performance," New Carbon Materials, vol. 32, No. 5, Oct. 2017, pp. 451-459.

Ren, Yi "Research Progress on Application of Nano Functional Materials in Glucose Detection," Chenmical Intermediate, Issue 10, Oct. 2018, pp. 7-8.

Zhao, Ting et al., "Carbon Nanotubes and Nickel Co-modified BDD Electrodes and Their Application for Non-enzymatic Glucose Electrochemical Sensor," Surface Technology, vol. 47, Issue 11, Nov. 2018, pp. 26-33.

Qin, Dong-Yu et al., "In Situ Preparation and Glucose Sensing Property of Ternary NiO/Ni/C Microspheres," Journal of Inorganic Materials, vol. 32, No. 3, Mar. 2017, pp. 313-318.

"International Search Report (Form PCT/ISA/210) of PCT/CN2021/091372," dated Aug. 3, 2021, pp. 1-6.

"Written Opinion of the International Searching Authority (Form PCT/ISA/237) of PCT/CN2021/091372," dated Aug. 3, 2021, pp. 1-5.

* cited by examiner

FIG. 9

FABRICATION METHOD OF ENZYME-FREE GLUCOSE SENSOR AND USE OF ENZYME-FREE GLUCOSE SENSOR FABRICATED BY THE SAME

CROSS-REFERENCE TO RELATED APPLICATION

This application is a 371 of international application of PCT application serial no. PCT/CN2021/091372, filed on Apr. 30, 2021, which claims the priority benefit of China application no. 202011013417.3, filed on Sep. 24, 2020. The entirety of each of the above mentioned patent applications is hereby incorporated by reference herein and made a part of this specification.

TECHNICAL FIELD

The present invention relates to the technical field of glucose detection, and in particular to an enzyme-free glucose sensor and a fabrication method and use thereof.

DESCRIPTION OF RELATED ART

Nickel-based materials are recognized as ideal electrocatalytic oxidants for glucose, and many studies on these materials have been reported. $Ni(OH)_2$ and NiO are favored by researchers due to their electrochemical stability, but they have low electrical conductivity. Nickel nanoparticles (Ni-NPs) have excellent electrical conductivity compared with $Ni(OH)_2$ and NiO, but are prone to agglomeration and deactivation during a catalytic process and have poor stability due to their characteristics such as small size and strong magnetism, which limits the further development of nickel nanoparticles for electrochemical catalysis in the field of nanomaterials. Over the past few decades, it has been expected to develop nickel nanoparticles with high stability and prominent electrical conductivity for electrochemical applications.

Nanostructured materials tend to have a large specific surface area (SSA) and thus can be used as highly-active adsorbents and catalysts. However, a process of synthesizing a nanomaterial is usually cumbersome and expensive. The synthesis of biomass-based nanomaterials is simple, economical, and environmentally friendly, and thus has received widespread attention. In addition, the original and unique structure of a biomass material is difficult to replicate through an experimental means, such as a three-dimensional (3D) layered structure that is beneficial to improve the ion transmission and storage performance of an electrode. For example, Bu Quan et al. (Chinese Patent No. 2020010657163.2) used biomass waste to prepare an electrochemical $H_2O_2$ sensor with excellent analytical performance. In addition, because carbon atoms and nitrogen atoms have similar radii, carbon atoms are easily replaced by nitrogen atoms. Previous studies have shown that nitrogen-doped carbon materials have better electrical conductivity and catalytic performance than carbon materials, and nitrogen doping is achieved in one step using ammonia etching.

Many scholars at home and abroad have conducted a lot of research on glucose electrical sensing. For example, Chinese patent CN 111537589 A discloses a method of using a cobalt-based metal-organic framework (MOF) material as an enzyme-free glucose sensor for detecting glucose, wherein the cobalt-based MOF material is prepared through distillation and synthesis, and a standard curve is plotted to determine a glucose content. The method involves single practice, has poor reproducibility, general application effect, low detection limit (1.6 μm/L), narrow linear range (5 μm/L to 900 μm/L), and low sensitivity (169 $\mu A \cdot mM^{-1} \cdot cm^{-2}$), and can only detect a glucose content, but cannot eliminate the influence of common interferents in a sample that are prone to electrooxidation, such as dopamine, ascorbic acid, and uric acid.

For example, Chinese patent CN 111505078 A discloses a Ni/Au composite nanowire array enzyme-free glucose sensor electrode and a fabrication method thereof, wherein an electrodeposition method is used to construct a double-layer nanowire structure from different electronegative noble metals and non-noble metals, and specifically, the noble metal Au is used, resulting in high fabrication cost. Moreover, the fabrication of the electrode takes a lot of time (6 h to 10 h), and an obtained electrode has narrow linear range (0.05 mM to 10 mM), low detection limit, and low reproducibility.

In previous studies, nanomaterials are usually fabricated by the template method, which is complicated and requires additional chemical reagents. CEM microwave synthesis has the advantages of simple operation, high efficiency, prominent reproducibility, no surface aggregation, extremely-clean surface, high stability, and the like, and thus is an effective synthesis method for inorganic nanomaterials. Moreover, electrochemical detection has attracted more and more attention due to advantages such as simple equipment, high sensitivity, low price, and high analysis speed. Glucose detection on traditional electrodes has a slow response of electrode materials, relies on oxidase molecules, and is easily affected by temperature and pH, which results in large errors in detection results. Another difficulty of electrochemical detection lies in the need to eliminate the influence of common interferents in a biological sample that are prone to electrooxidation, such as dopamine, ascorbic acid, and uric acid. Therefore, it is necessary to propose an effective technical solution to solve the above-mentioned problems.

SUMMARY

In order to solve the above technical deficiencies, the present invention provides an enzyme-free glucose sensor based on a biomass composite nano-electrode material Ni@NSiC and a detection method using the same. A highly-active material-modified electrode fabricated by this method can be effectively used for high-sensitivity and selective detection of glucose in the presence of interferents (dopamine, ascorbic acid, uric acid, and the like).

A fabrication method of an enzyme-free glucose sensor based on a biomass composite nano-electrode material Ni@NSiC is provided, comprising the following steps.

Step (1): subjecting washed and dried *Magnolia grandiflora* L. leaves to calcination in a high-temperature tube furnace to obtain biochar for later use.

Step (2): adding hydrochloric acid-treated biochar, pyromellitic acid, nickel acetylacetonate, and N,N-dimethylformamide (DMF) to a mixed solution of ethanol and ultrapure water (UPW), and stirring a resulting mixture for dispersion to obtain a mixed solution A.

Step (3): subjecting the mixed solution A to a complete reaction in a CEM microwave synthesizer to obtain a mixed solution precursor B.

Step (4): pouring the cooled mixed solution precursor B into a centrifuge tube, washing, centrifuging, and drying to obtain a product C.

Step (5): subjecting the product C to high-temperature calcination at 900° C. for 2 h under an $NH_3$ atmosphere in the high-temperature tube furnace to obtain a pure-phase Ni@NSiC nano-electrode composite material.

Step (6): weighing an appropriate amount of the Ni@NSiC nano-electrode composite material to prepare a Ni@NSiC solution using water, ethanol, and a 5% Nafion solution for later use, pipetting the Ni@NSiC solution with a pipette and adding dropwise onto a pretreated electrode, and air-drying the electrode to obtain a highly-active material-modified electrode Ni@NSiC/GCE.

In step (1), the calcination in the high-temperature tube furnace is conducted under the following process parameters: $N_2$ atmosphere; heating rate: 5° C./min; reaction temperature: 600° C.; reaction time: 2 h; and $N_2$ flow rate: 0.5 L/min.

In step (2), the biochar is soaked in 0.5 M/L hydrochloric acid for 12 h, then filtered out, and dried for later use; in the mixed solution A, the hydrochloric acid-treated biochar, the pyromellitic acid, the nickel acetylacetonate, the DMF, the ethanol, and the UPW have a ratio of 0.04 g:0.2542 g:0.2569 g:5 ml:10 ml; and in the mixed solution of ethanol and UPW, a volume ratio of the ethanol to the UPW is 1:1.

In step (3), a microwave reaction is conducted under the following process parameters: a microwave power: 180 W to 200 W, a reaction temperature: 160° C. to 180° C., and a reaction time: 2 h.

In step (5), a flow rate of the $NH_3$ is 0.1 L/min.

In step (6), in the Ni@NSiC solution, the Ni@NSiC nano-electrode composite material has a concentration of 5 mg/mL, and the water, the ethanol, and the 5% Nafion solution have a volume ratio of 665 μL:335 μL:25 μL; and 5 μL of the Ni@NSiC solution is pipetted with the pipette.

Preferably, the pretreated electrode is prepared by polishing a glassy carbon electrode (GCE) successively with 1.0 μm, 0.3 μm, and 0.05 μm $Al_2O_3$ polishing powders; rinsing the GCE with deionized water, and subjecting the GCE to ultrasonic treatment three times with deionized water and then to ultrasonic treatment once with absolute ethanol, wherein each ultrasonic treatment is conducted for no more than 30 s; and finally blow-drying the GCE with nitrogen for later use.

Use of the enzyme-free glucose sensor based on a biomass composite nano-electrode material Ni@NSiC in high-sensitivity detection of glucose is provided.

Preferably, a glucose detection method uses cyclic voltammetry (CV), chronoamperometry (CA), and a three-electrode system; the three-electrode system is composed of a working electrode, a reference electrode, and a counter electrode; the working electrode is the highly-active material-modified electrode Ni@NSiC/GCE fabricated, the reference electrode is an Ag/AgCl electrode, and a platinum wire is used as the counter electrode; and a 0.1 M NaOH solution is used as an initial base solution.

Preferably, parameters for the CA are set as follows: test potential: 0.5 V; time: 3,600 s; and after an electrical signal is stable, taking 2 μL of each of glucose solutions at different concentrations using a microliter syringe and adding into a weighing bottle, and starting from 400 s, at an interval of 50 s, adding 0.25 μM/L glucose once, adding each of 0.5 μM/L, 1 μM/L, 2 μM/L, 5 μM/L, 10 μM/L, 20 μM/L, 50 μM/L, 100 μM/L, and 200 μM/L glucose three times, and adding 500 μM/L glucose until a cascade effect is not obvious; linear ranges are 0.5 μM to 1,145.75 μM ($R^2$=0.9932, I/μA=10.11455+0.01995×C/μM) and 1,645.75 μM to 8,145.75 μM ($R^2$=0.9983, I/μA=25.47582+0.00731×C/μM), and the lowest detection limit is 0.125 μM (S/N=3).

The principle of the present invention is as follows.

$$Ni+2OH^{-1}=Ni(OH)_2+2e^- \quad (1)$$

$$Ni(OH)_2+OH^-=NiO(OH)+H_2O+e^- \quad (2)$$

A Ni atom loses two electrons under alkaline conditions to form $Ni(OH)_2$, and then $Ni(OH)_2$ loses one electron under alkaline conditions to form NiO(OH) and $H_2O$, which increases active sites and greatly improves the electrocatalytic effect for glucose.

Beneficial Effects

An electrode modified by the material synthesized by the method of the present invention has a pair of obvious redox peaks that are relatively symmetrically distributed, and shows high sensitivity. The fabrication method is simple and stable.

The electrode modified by the Ni@NSiC nano-electrode composite material synthesized by the present invention can not only catalyze the oxidation of glucose, but also catalyze the reduction of its oxidation product. In addition, compared with traditional electrochemical redox, the nanomaterial prepared by this method can be used to eliminate the influence of common interferents in a biological sample that are prone to electrooxidation, such as dopamine, ascorbic acid, and uric acid.

DESCRIPTION OF THE EMBODIMENTS

Example 1

A fabrication method of an enzyme-free glucose sensor based on a biomass composite nano-electrode material Ni@NSiC was provided, comprising the following steps.

Washed and dried *Magnolia grandiflora* L. leaves were subjected to calcination at 600° C. for 2 h under a $N_2$ (0.5 L/min) atmosphere in a high-temperature tube furnace to obtain biochar for later use.

0.04 g of 0.5 M/L hydrochloric acid-treated biochar, 0.2542 g of pyromellitic acid, 0.2569 g of nickel acetylacetonate, and 5 ml of DMF were added to 10 ml of an ethanol/UPW (1:1) mixed solution, and a resulting mixture was stirred for 30 min to obtain a mixed solution A.

The mixed solution A was subjected to a complete reaction in a CEM microwave synthesizer under the following conditions to obtain a mixed solution precursor B: reaction temperature: 180° C., reaction time: 2 h, and microwave power: 200 W.

The cooled mixed solution precursor B was poured into a centrifuge tube, washed, centrifuged, and dried to obtain a product C.

The product C was subjected to high-temperature calcination at 900° C. for 2 h under an ammonia gas atmosphere (0.1 L/min) in a tube furnace to obtain a pure-phase Ni@NSiC nano-electrode composite material.

5 mg of the synthesized Ni@NSiC nano-electrode composite material was weighed and prepared into a Ni@NSiC solution using 665 μL of deionized water, 335 μL of ethanol, and 24 μL of 5% Nafion for later use, 5 μL of the Ni@NSiC solution was pipetted with a pipette and added dropwise onto a pretreated electrode, and the electrode was air-dried to obtain a highly-active material-modified electrode Ni@NSiC/GCE.

In the electrode Ni@NSiC/GCE fabricated by the above method, nickel atoms are uniformly distributed on a surface of a carbon material prepared, which overcomes the defects of easy aggregation of metal atoms and little active sites. An active site in which a nickel atom is located can not only catalyze the oxidation of glucose, but also catalyze the reduction of its oxidation product. In addition, the electrode material fabricated by the above method can highly sensitively detect glucose without requiring many active sites, which lays a foundation for subsequent electrochemical recognition.

The highly-electroactive material-modified electrode Ni@NSiC/GCE obtained in Example 1 was characterized by XRD, SEM, TEM, CV, CA, and other techniques.

Figure 1:
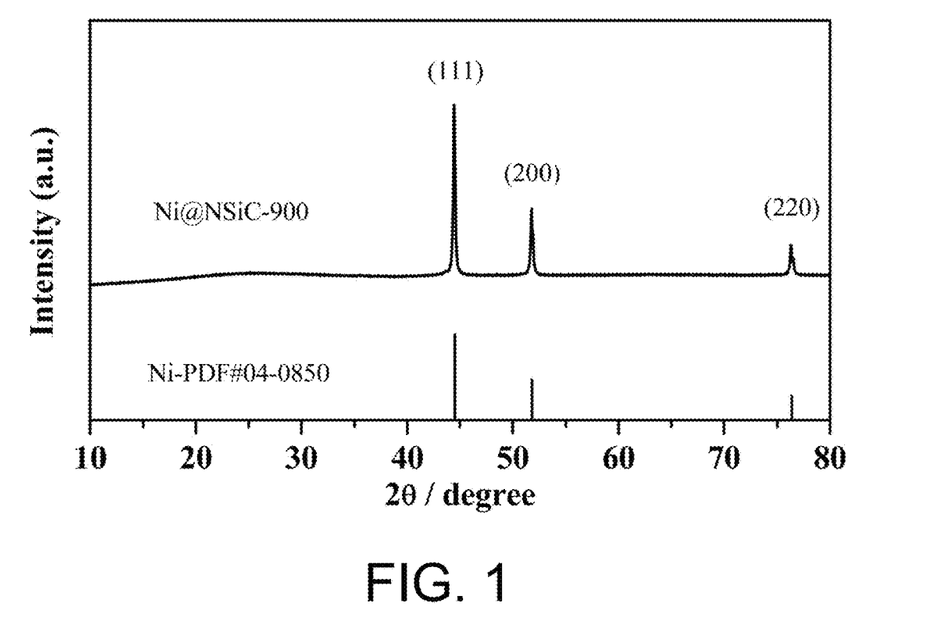
FIG. 1 shows an X-ray diffractometry (XRD) pattern of Ni@NSiC.

FIG. 1 shows an XRD pattern of Ni@NSiC. It can be seen from the figure that the synthesized substance is a pure phase, without other impurity peaks; and peaks corresponding to the standard card Ni-PDF #04-0850 are three crystal planes (111), (200), and (220) of nickel atom.

Figure 2:
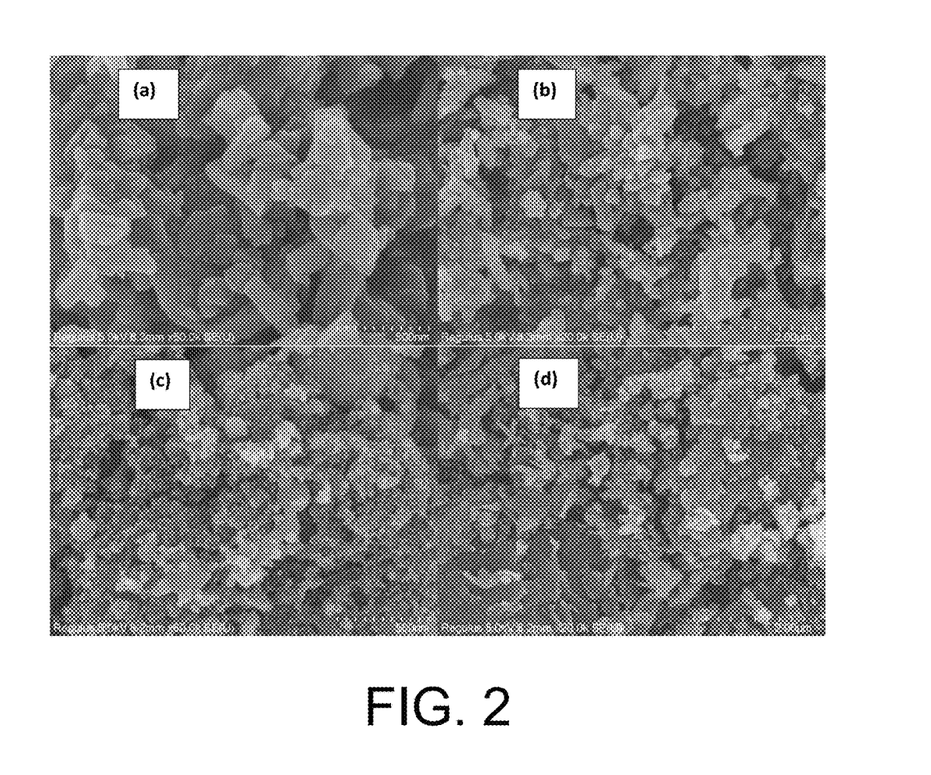
FIG. 2 shows scanning electron microscopy (SEM) images of Ni@NSiC, wherein (a) and (b) of FIG. 2 are SEM images before calcination, and (c) and (d) of FIG. 2 are SEM images after calcination.

FIG. 2 shows SEM images of Ni@NSiC before calcination ((a) and (b) of FIG. 2) and after calcination ((c) and (d) of FIG. 2) according to the present invention. It can be seen from the figure that the morphology changes a lot before and after calcination; before calcination, a structure of Ni@NSiC is mostly columnar; and after calcination, many nickel particles are attached to a meshed carbon surface, which provides many active sites and is conducive to the electrocatalysis for glucose.

Figure 3:
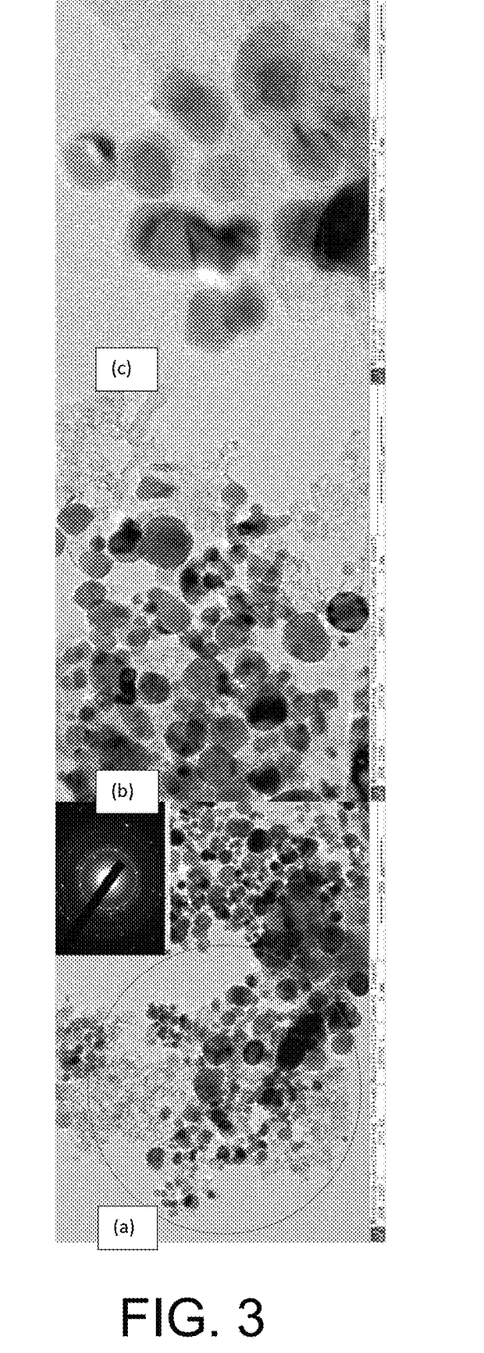
FIG. 3 shows transmission electron microscopy (TEM) images of Ni@NSiC, wherein (a), (b), and (c) of FIG. 3 are TEM images at different magnifications.

FIG. 3 shows TEM images of Ni@NSiC after calcination, wherein image (a) is an HRTEM image, image (b) is a 100 nm TEM image, and image (c) is a 20 nm TEM image. It can be seen from figure that many nickel atom particles are uniformly distributed on a carbon surface, with excellent morphology.

Figure 4:
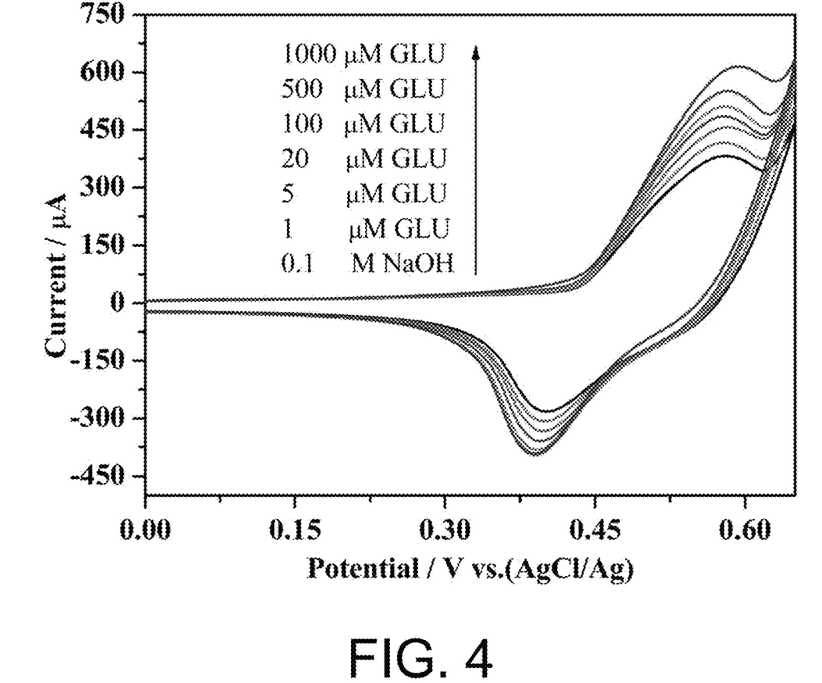
FIG. 4 shows cyclic voltammograms of Ni@NSiC/GCE at different glucose concentrations.

FIG. 4 shows cyclic voltammograms of Ni@NSiC at different glucose concentrations, wherein the cyclic voltammograms of the Ni@NSiC/GCE electrode in 0 μM, 1 μM, 5 μM, 20 μM, 100 μM, 500 μM, and 1,000 μM glucose solutions are showed from bottom to top according to oxidation peaks. It can be seen from the figure that the Ni@NSiC/GCE electrode has a high electrochemical response to glucose solutions, with an obvious oxidation peak at about 0.52 V and a strong reduction peak at about 0.37 V; the redox peaks have prominent symmetry; and with the linear increase of glucose concentration, the redox peaks increase linearly, indicating that the Ni@NSiC material has a prominent electrocatalytic effect for glucose.

Figure 5:
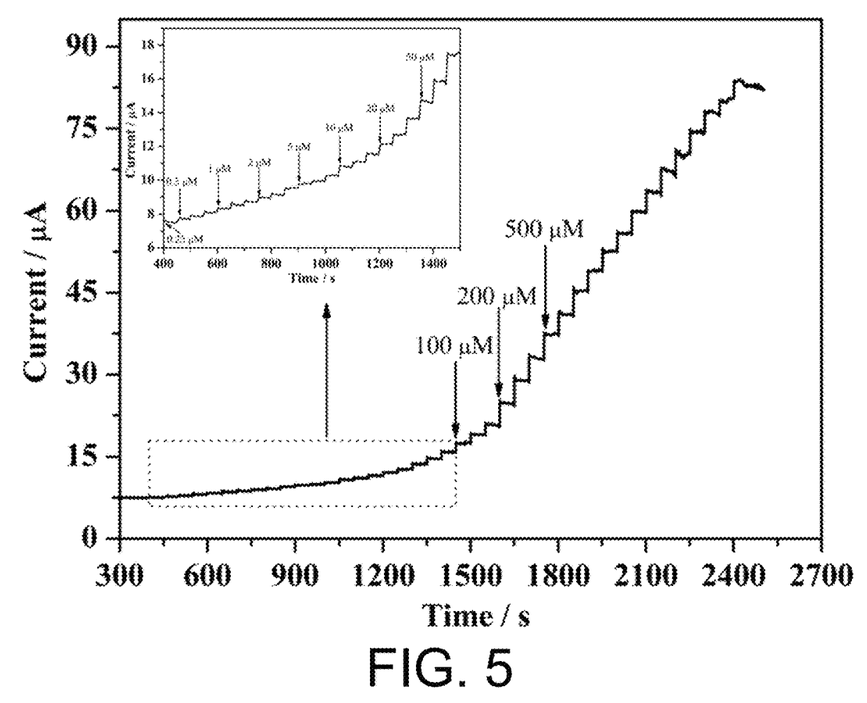
FIG. 5 shows an i-t response graph of Ni@NSiC/GCE when glucose solutions with different concentrations are added at 0.5 V.

FIG. 5 shows an i-t response graph of Ni@NSiC/GCE when glucose solutions with different concentrations are added at 0.5 V. According to the response of CV, the electrode shows the optimal i-t linearity at 0.5 V. During an i-t test, each of glucose solutions with different concentrations is added to a weighing bottle every 50 s at room temperature and atmospheric pressure, and it can be known from the experiment that the lowest detection limit is 0.125 μM (S/N=3).

Figure 6:
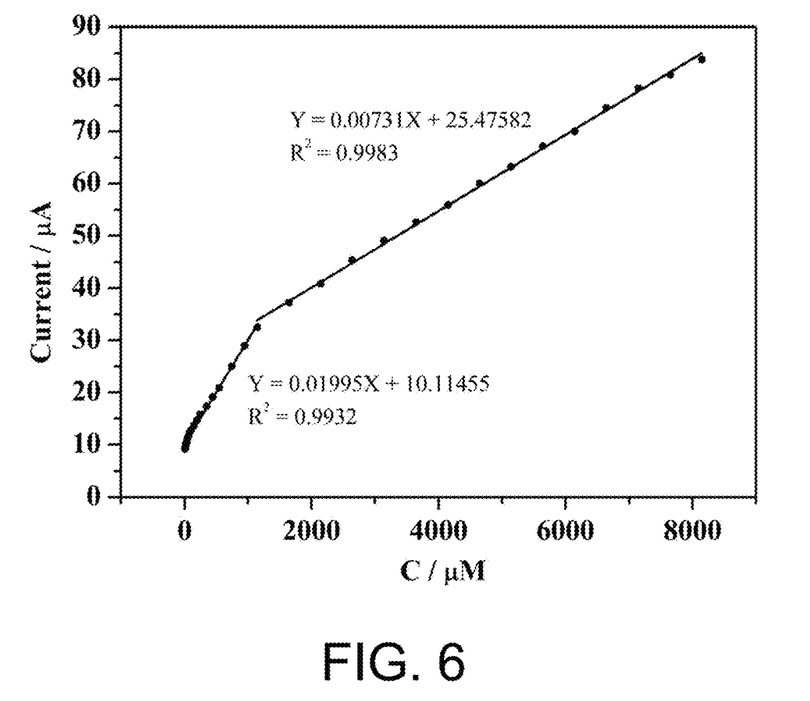
FIG. 6 shows an i-t linear response graph of Ni@NSiC/GCE when glucose solutions with different concentrations are added at 0.5 V.

FIG. 6 shows an i-t step linear response graph of Ni@NSiC/GCE when glucose solutions with different concentrations are added at 0.5 V. The current response increases linearly with the increase of glucose concentration, and a linear regression equation of the glucose sensor can be set as: $I/\mu A=10.11455+0.01995 \times C/\mu M (R^2=0.9932)$ and $I/\mu A=25.47582+0.00731 \times C/\mu M (R^2=0.9983)$.

Figure 7:
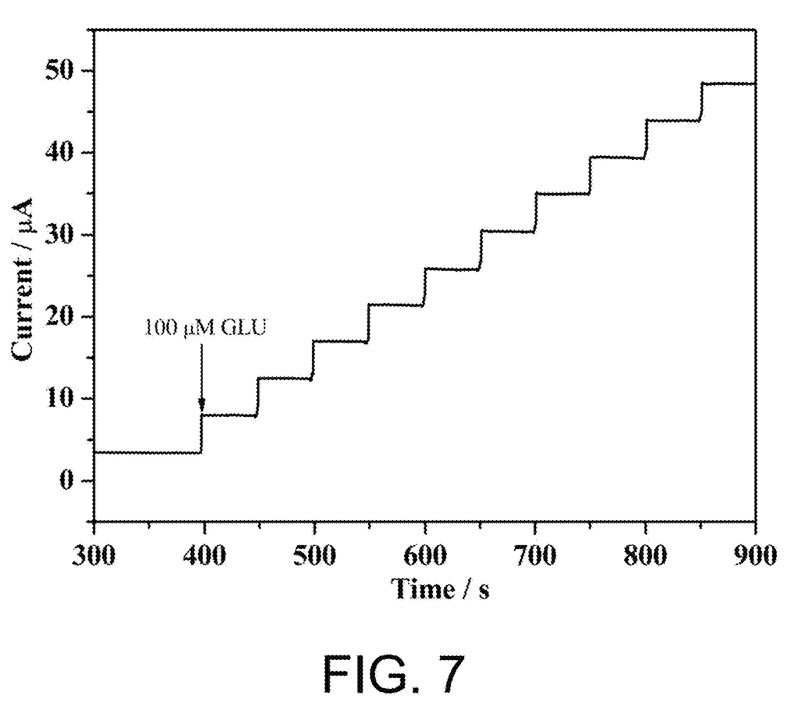
FIG. 7 shows a reproducibility-current response graph of Ni@NSiC/GCE at 0.5 V.

FIG. 7 shows a reproducibility-current response graph of Ni@NSiC/GCE at 0.5 V. The figure shows reproducibility results obtained by continuously adding a 0.1 mM/L glucose solution dropwise every 50 s on the Ni@NSiC/GCE electrode at a potential of 0.5 V starting from 400 s, indicating that the glucose detection has prominent reproducibility. The fabricated electrode material has high activity and can be reused many times.

Figure 8:
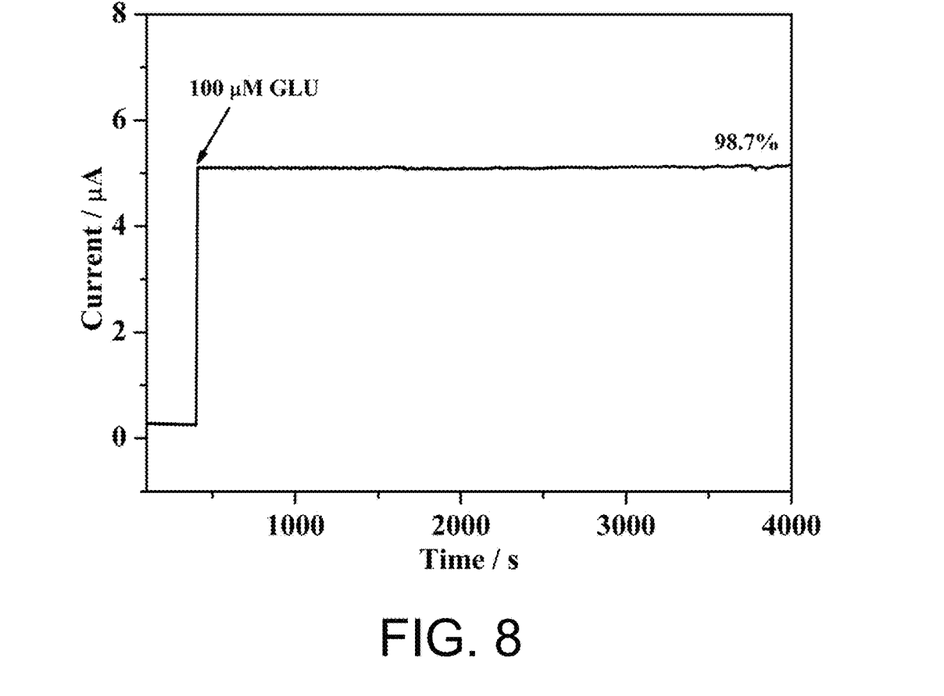
FIG. 8 shows a stability-current response graph of Ni@NSiC/GCE at 0.5 V.

FIG. 8 shows a stability-current response graph of Ni@NSiC/GCE at 0.5 V. The stability of the Ni@NSiC/GCE sensing material was tested by an i-t test at an electrochemical workstation. 2 μL of a 100 μM/L glucose solution was added at 400 s, at which point the base solution was 0.1 M/L NaOH-100 μM/L glucose; and then the sensing material was allowed to stand for 3,600 s. Results show that the Ni@NSiC/GCE has high stability. From the ampere response measured with a 100 μM/L glucose solution, it can be seen that, after 3,600 s, the peak current of the 100 μM/L glucose on the Ni@NSiC/GCE electrode still retained 98.7% of the initial value, indicating that the Ni@NSiC/GCE electrode has excellent stability.

Figure 9:
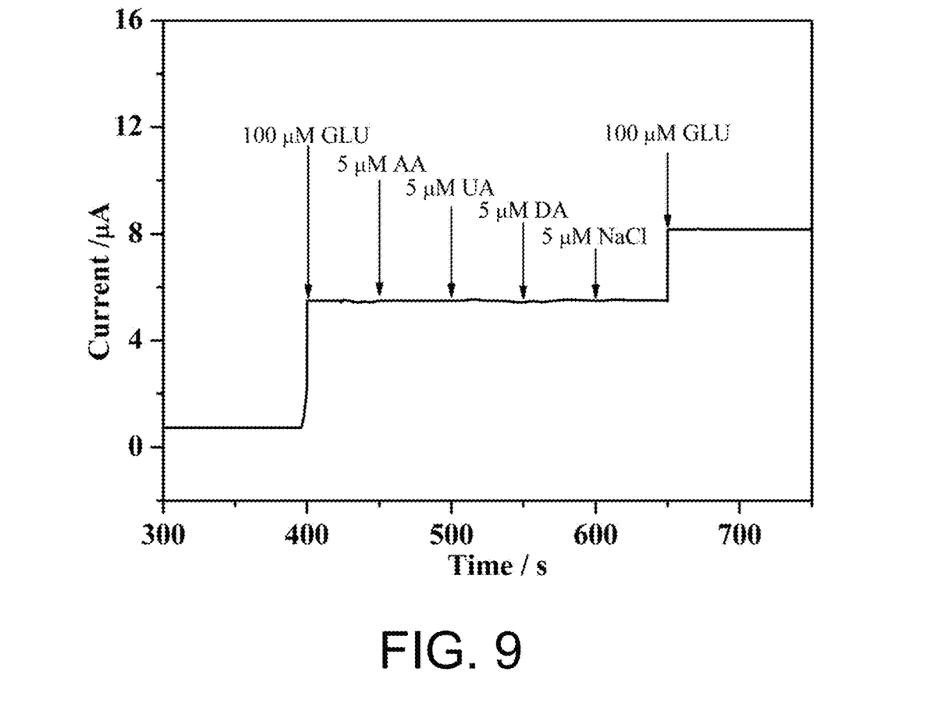
FIG. 9 shows an anti-interference-current response diagram of common interferents on Ni@NSiC/GCE.

FIG. 9 shows an anti-interference response diagram of common interferents on Ni@NSiC/GCE. In 0.1 M/L NaOH, a total of 4 interferents (5 μM/L AA, UA, DA, and NaCl) were added successively to conduct an anti-interference test on the Ni@NSiC/GCE electrode through i-t at a sweep rate of 0.1 V/s. These substances basically do not have the electrocatalytic oxidation effect similar to that of glucose and thus basically have no interference effect for the glucose solution, and the stability is also high after glucose is added once again.

Sources of the reagents mentioned in the present invention: pyromellitic acid, uric acid, dopamine hydrochloride, cysteine, and ascorbic acid were purchased from Aladdin Reagent Co., Ltd.; glucose, sodium chloride, and DMF were purchased from Sinopharm Group Chemical Reagent Co., Ltd.; nickel acetylacetonate and sodium hydroxide were purchased from Sigma-Aldrich; *Magnolia grandiflora* L. leaves were picked from the campus of Jiangsu University; and GCE (3 mm) was purchased from Wuhan GaossUnion Technology Co., Ltd.

What is claimed is:

1. A fabrication method of an enzyme-free glucose sensor, comprising the following specific steps:
   step (1): subjecting washed and dried *Magnolia grandiflora* L. leaves to calcination in a high-temperature tube furnace to obtain a biochar;
   step (2): soaking the biochar in hydrochloric acid, adding the hydrochloric acid-treated biochar, pyromellitic acid, nickel acetylacetonate, and N,N-dimethylformamide to a mixed solution of ethanol and ultrapure water to obtain a resulting mixture, and stirring the resulting mixture for dispersion to obtain a mixed solution A;

step (3): subjecting the mixed solution A to a reaction in a microwave synthesizer to obtain a mixed solution precursor B, wherein the reaction in the step (3), the reaction in the microwave synthesizer is conducted under the following process parameters: a microwave power: 180 W to 200 W, a reaction temperature: 160° C. to 180° C., and a reaction time: 2 h;

step (4): pouring the mixed solution precursor B into a centrifuge tube, then centrifuging and drying the mixed solution precursor B to obtain a product C;

step (5): flowing $NH_3$ in the high-temperature tube furnace and subjecting the product C to high-temperature calcination at 900° C. for 2 h in the high-temperature tube furnace to obtain a Ni@NSiC nano-electrode composite material; and step (6): mixing the Ni@NSiC nano-electrode composite material, water, ethanol, and a 5 wt % Nafion solution to prepare a Ni@NSiC solution, pipetting the Ni@NSiC solution with a pipette and adding dropwise onto a pretreated electrode, and air-drying the electrode to obtain a Ni@NSiC/GCE electrode, wherein in the step (6), in the Ni@NSiC solution, the Ni@NsiC nano-electrode composite material has a concentration of 5 mg/mL, and the water, the ethanol, and the 5 wt % Nafion solution have a volume ratio of 665 µL:335 µL:25 µL; 5 µL of the Ni@NsiC solution is pipetted with the pipette; and the pretreated electrode is prepared by polishing a glassy carbon electrode (GCE) successively with 1.0 µm, 0.3 µm, and 0.05 µm $Al_2O_3$ polishing powders; rinsing the GCE with deionized water, and subjecting the GCE to ultrasonic treatment three times with deionized water and then to ultrasonic treatment once with absolute ethanol, wherein each ultrasonic treatment is conducted for no more than 30 s; and finally blow-drying the GCE with nitrogen.

2. The fabrication method of the enzyme-free glucose sensor according to claim 1, wherein in the step (1), the calcination in the high-temperature tube furnace is conducted under the following process parameters: a $N_2$ atmosphere; a heating rate: 5° C./min; a calcination temperature: 600° C.; a calcination time: 2 h; and a $N_2$ flow rate: 0.5 L/min.

3. An use of the enzyme-free glucose sensor fabricated by the fabrication method according to claim 2 in high-sensitivity detection of glucose, wherein the glucose detection uses cyclic voltammetry, chronoamperometry, and a three-electrode system; the three-electrode system is composed of a working electrode, a reference electrode, and a counter electrode; the working electrode is the Ni@NSiC/GCE electrode, the reference electrode is an Ag/AgCl electrode, and a platinum wire is used as the counter electrode; and a 0.1 M NaOH solution is used as an electrolyte, wherein the enzyme-free glucose sensor is the Ni@NSiC/GCE electrode.

4. The fabrication method of the enzyme-free glucose sensor according to claim 1, wherein in the step (2), the biochar is soaked in 0.5 M/L hydrochloric acid for 12 h, then filtered out, and dried; in the mixed solution A, the hydrochloric acid-treated biochar, the pyromellitic acid, the nickel acetylacetonate, the N,N-dimethylformamide, the ethanol, and the ultrapure water have a ratio of 0.04 g:0.2542 g:0.2569 g:5 ml:10 ml; and in the mixed solution of ethanol and ultrapure water, a volume ratio of the ethanol to the ultrapure water is 1:1.

5. An use of the enzyme-free glucose sensor fabricated by the fabrication method according to claim 4 in high-sensitivity detection of glucose, wherein the glucose detection uses cyclic voltammetry, chronoamperometry, and a three-electrode system; the three-electrode system is composed of a working electrode, a reference electrode, and a counter electrode; the working electrode is the Ni@NSiC/GCE electrode, the reference electrode is an Ag/AgCl electrode, and a platinum wire is used as the counter electrode; and a 0.1 M NaOH solution is used as an electrolyte, wherein the enzyme-free glucose sensor is the Ni@NSiC/GCE electrode.

6. The fabrication method of the enzyme-free glucose sensor according to claim 1, wherein in the step (5), a flow rate of the $NH_3$ is 0.1 L/min.

7. An use of the enzyme-free glucose sensor fabricated by the fabrication method according to claim 6 in high-sensitivity detection of glucose, wherein the glucose detection uses cyclic voltammetry, chronoamperometry, and a three-electrode system; the three-electrode system is composed of a working electrode, a reference electrode, and a counter electrode; the working electrode is the Ni@NSiC/GCE electrode, the reference electrode is an Ag/AgCl electrode, and a platinum wire is used as the counter electrode; and a 0.1 M NaOH solution is used as an electrolyte, wherein the enzyme-free glucose sensor is the Ni@NSiC/GCE electrode.

8. An use of the enzyme-free glucose sensor fabricated by the fabrication method according to claim 1 in high-sensitivity detection of glucose, wherein the glucose detection uses cyclic voltammetry, chronoamperometry, and a three-electrode system; the three-electrode system is composed of a working electrode, a reference electrode, and a counter electrode; the working electrode is the Ni@NSiC/GCE electrode, the reference electrode is an Ag/AgCl electrode, and a platinum wire is used as the counter electrode; and a 0.1 M NaOH solution is used as an electrolyte, wherein the enzyme-free glucose sensor is the Ni@NSiC/GCE electrode.

\* \* \* \* \*